United States Patent
Eckey et al.

(10) Patent No.: US 10,190,943 B2
(45) Date of Patent: Jan. 29, 2019

(54) METHOD AND DEVICE FOR INSPECTING ROLLING ELEMENTS BY MEANS OF ULTRASOUND

(71) Applicants: THYSSENKRUPP ROTHE ERDE GMBH, Dortmund (DE); ALTHAUS ENGINEERING, Büren (DE)

(72) Inventors: Martin Eckey, Lippstadt (DE); Heiko Althaus, Büren (DE); Marco Burtchen, Lippstadt (DE)

(73) Assignees: ThyssenKrupp Rothe Erde GmbH, Dortmund (DE); Althaus Engineering, Büren (DE)

( * ) Notice: Subject to any disclaimer, the term of this patent is extended or adjusted under 35 U.S.C. 154(b) by 194 days.

(21) Appl. No.: 14/905,466

(22) PCT Filed: Jul. 15, 2014

(86) PCT No.: PCT/EP2014/065088
§ 371 (c)(1),
(2) Date: Jan. 15, 2016

(87) PCT Pub. No.: WO2015/007708
PCT Pub. Date: Jan. 22, 2015

(65) Prior Publication Data
US 2016/0169770 A1    Jun. 16, 2016

(30) Foreign Application Priority Data
Jul. 16, 2013    (DE) .................. 10 2013 107 560

(51) Int. Cl.
*G01M 13/04*    (2006.01)
*G01N 29/27*    (2006.01)
(Continued)

(52) U.S. Cl.
CPC ........ *G01M 13/045* (2013.01); *G01N 29/041* (2013.01); *G01N 29/225* (2013.01);
(Continued)

(58) Field of Classification Search
CPC .. G01M 13/045; G01M 13/04; G01N 29/041; G01N 29/225; G01N 29/27; G01N 29/28;
(Continued)

(56) References Cited

U.S. PATENT DOCUMENTS

| | | | | |
|---|---|---|---|---|
| 3,803,904 A | * | 4/1974 | Diem | G01N 29/26 73/640 |
| 4,969,361 A | * | 11/1990 | Kawasaki | G01N 29/26 209/538 |

(Continued)

FOREIGN PATENT DOCUMENTS

| | | |
|---|---|---|
| DE | 266848 A1 | 4/1989 |
| DE | 3905430 A1 | 11/1989 |

(Continued)

OTHER PUBLICATIONS

International Preliminary Report on Patentability, Application No. PCT/EP2014/065088 dated Jan. 19, 2016.
(Continued)

*Primary Examiner* — Manish S Shah
*Assistant Examiner* — Rose M Miller
(74) *Attorney, Agent, or Firm* — The Dobrusin Law Firm, P.C.

(57) ABSTRACT

The invention concerns a method for inspection of rolling elements (W) by means of ultrasound, wherein the rolling elements (W) are taken individually to an ultrasound measuring device (4), wherein the rolling elements (W) are moved in the ultrasound measuring device (4) and subjected to an ultrasound measurement and wherein depending on a result of the ultrasound measurement the individual rolling
(Continued)

Figure 1:
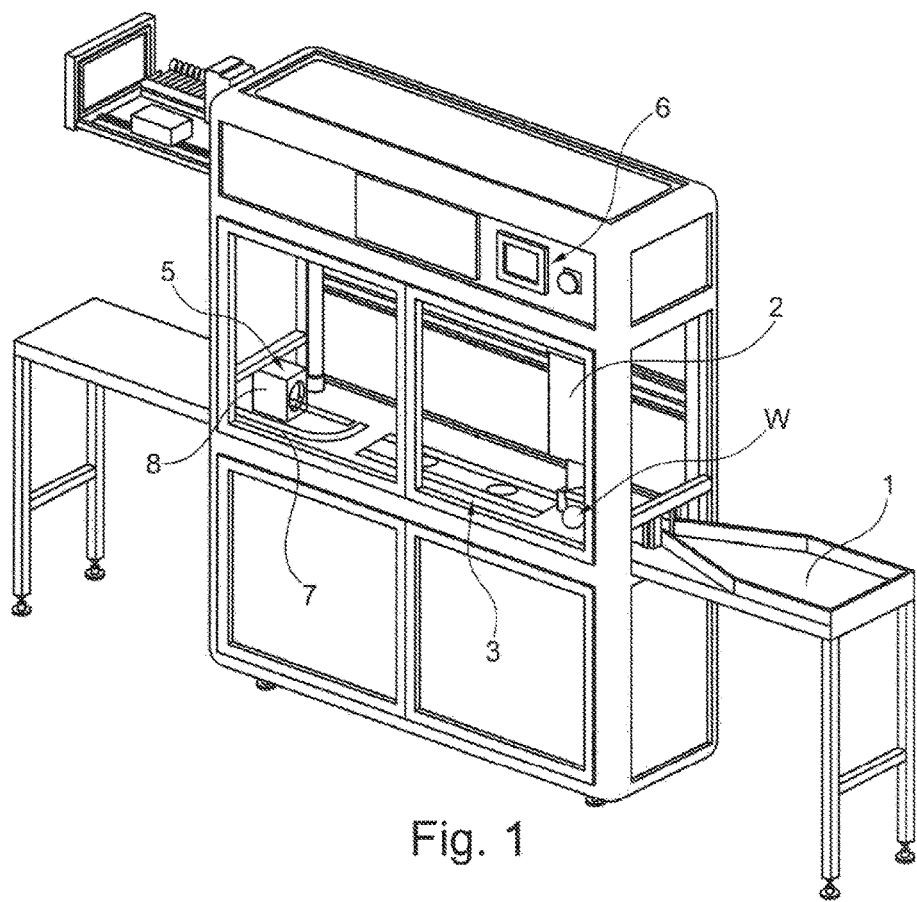

elements (W) are classified as defective or nondefective. The subject matter of the invention is also a rolling element inspection layout for performance of the method, having at least one ultrasound measuring device (4) with a holder for the individual rolling elements (W), at least one ultrasound head (10) and a drive unit for the movement of the individual rolling elements (W).

16 Claims, 2 Drawing Sheets

(51) Int. Cl.
  *G01N 29/04* (2006.01)
  *G01N 29/22* (2006.01)
  *G01N 29/28* (2006.01)
(52) U.S. Cl.
  CPC .............. *G01N 29/27* (2013.01); *G01N 29/28* (2013.01); *G01N 2291/105* (2013.01); *G01N 2291/265* (2013.01); *G01N 2291/2696* (2013.01)
(58) Field of Classification Search
  CPC ...... G01N 29/04; G01N 29/043; G01N 29/22; G01N 29/275; G01N 2291/105; G01N 2291/2696; G01N 2291/265
  USPC ......... 73/593, 618, 620, 621, 624, 627, 633, 73/640
  See application file for complete search history.

(56) References Cited

U.S. PATENT DOCUMENTS

| | | | |
|---|---|---|---|
| 5,184,513 A * | 2/1993 | Nishioka | G01N 29/27 294/104 |
| 5,195,372 A | 3/1993 | Fushimi et al. | |
| 5,223,793 A * | 6/1993 | Ricci | G01M 13/04 324/226 |
| 2007/0289385 A1 | 12/2007 | Kiuchi | |
| 2009/0019937 A1 | 1/2009 | Deemer et al. | |
| 2013/0269435 A1 * | 10/2013 | Jauriqui | G01N 29/041 73/579 |

FOREIGN PATENT DOCUMENTS

| | | |
|---|---|---|
| DE | 69023867 T2 | 6/1996 |
| DE | 69025037 T2 | 9/1996 |
| DE | 102004023871 A1 | 12/2005 |
| EP | 0625703 A1 | 11/1994 |
| EP | 1475633 A1 | 11/2004 |
| JP | 2010127621 A | 6/2010 |
| RU | 2334665 C1 | 9/2008 |

OTHER PUBLICATIONS

International Search Report and Written Opinion, Application No. PC/EP2014/065088 dated Dec. 16, 2014.

\* cited by examiner

METHOD AND DEVICE FOR INSPECTING ROLLING ELEMENTS BY MEANS OF ULTRASOUND

The invention concerns a method for inspection of rolling elements by means of ultrasound as well as a rolling element inspection layout with an electronic control unit and at least one ultrasound measuring device.

It is known from practice how to inspect structural parts for material defects by means of ultrasound in a nondestructive manner, the ultrasound being conducted into the material across a surface being inspected and defects on the surface of the structural part and in the material of the structural part altering the acoustical properties, especially the reflection of the ultrasound waves. Besides surface cracks and defects, it is also possible to detect defects, voids, inclusions or texture deviations in the volume of the material. Ultrasound inspection is often used for uniform surfaces, especially pipes or the like.

It is known from US 2007/0289385 A1 how to inspect the running surface of a roller bearing with ultrasound. An inspection of the running surface is possible prior to assembly of the roller bearing or after the roller bearing is taken apart during maintenance.

The running surfaces of a roller bearing are subjected to considerable loads during the intended use of the roller bearing, while a certain amount of wear is usual. Thus, it is known that typical usage marks occur on the running surfaces of a roller bearing, making it possible to evaluate the wear. On the other hand, the defects which can be identified by ultrasound carry the danger of a sudden impairment of the bearing properties.

A layout is known from DD 266848 A1 for the inspection of roller bearing outer races and rollers, which combines an ultrasound measuring device with other measuring devices. The assessment of the roller bearing is based on all the signals obtained from the different measuring devices. DD 266848 A1 deals specifically with the inspection of wheel set roller bearings, which cannot be disassembled entirely into their individual parts without considerable expense. Therefore, a combined measurement of various parameters is performed on the outer race with the rollers running inside it, and if cracks are detected beneath or on the rolling surfaces of the outer race and the rollers the corresponding roller bearing is rejected as defective. The combination of different measurement methods has the advantage that a comparison of the different signals can achieve a greater accuracy and certainty. In particular, a reliable coupling of the ultrasound into the parts of the roller bearing is difficult, since the running surfaces are only partially accessible. Cracks or defects on the side surfaces of the rolling elements configured as rollers cannot be detected.

Given this context, the problem which the present invention proposes to solve is to accomplish an increased degree of certainty against malfunctions in the production or maintenance of roller bearings with simple means.

The subject matter of the invention and the solution of the problem are: a method for the inspection of rolling elements by means of ultrasound, wherein the rolling elements are taken individually to an ultrasound measuring device, wherein the rolling elements are moved in the ultrasound measuring device and subjected to an ultrasound measurement, and wherein depending on a result of the ultrasound measurement the individual rolling elements are classified as defective or nondefective: and a rolling element inspection layout with an electronic control unit and at least one ultrasound measuring device, characterized in that the ultrasound measuring device has a holder for individual rolling elements, at least one ultrasound head connected to the electronic control unit, and a drive unit for the movement of the individual rolling elements.

According to the invention, an inspection of rolling elements s done by means of ultrasound, wherein the rolling elements are taken individually to an ultrasound measuring; device, wherein the rolling elements are moved in the ultrasound measuring device and subjected to an ultrasound measurement and wherein depending on a result of the ultrasound measurement the individual rolling elements are classified as defective or nondefective.

Whereas in the prior art an inspection of the running races or of the entire roller bearing is done, the present invention is based on the notion that the individual rolling elements can also constitute a not insignificant defect source for material or surface defects. The present invention therefore teaches an individual inspection of the individual rolling elements before they are installed for the first time or again during maintenance in a roller bearing. Since the rolling elements are subjected individually to an ultrasound measurement, the entire surface is freely accessible, so that a comprehensive and especially reliable inspection can take place.

In order to survey the entire surface of the rolling elements various methods, are possible which can also be combined with each other.

For example, at least two ultrasound heads can be provided in the ultrasound measuring device, with which the rolling elements are examined. The at least two ultrasound heads can be arranged so that different regions of the rolling elements are inspected each time, preferably the entire surface of the rolling element.

Furthermore, it is also possible to turn the rolling elements in different directions during their individual examination in the ultrasound measuring device during the measurement process, for example so that a tumbling or meandering movement is the result. For example, a rolling element can be moved in the ultrasound measuring device so that the entire surface is moved consecutively past an ultrasound head.

Especially preferred is a combination of the two described techniques, wherein at least two ultrasound measuring heads are used and the rolling elements are turned in different directions.

For example, according to one preferred embodiment of the invention, when rolling elements in spherical shape are brought up for inspection, these can be set down in the ultrasound measuring device on two noncylindrical drive rollers. Then, if the drive rollers are actuated variably and not synchronized, a tumbling or meandering movement will result.

Basically, different movement profiles are conceivable. If, for example, two conical or truncated conical drive rollers of the same size are used, a rolling element of spherical shape will be arranged in the center between the two drive rollers. If the drive rollers are then turned with the same speed and in the same direction about a common axis of rotation, the rolling element placed thereupon will also turn about an axis arranged parallel to the axis of rotation of the drive rollers, so that a circumferential line of the rolling element of spherical shape will be moved past a stationary ultrasound head. After a complete rotation, an opposite running drive unit of the two drive rollers can produce a rotation of the sphere about a vertical axis, and then during another synchronous rotation a different circumferential line in the manner of a meridian is moved past the assigned measuring device.

In particular, when several ultrasound heads are used, an especially rapid inspection and surveying of the entire volume can be achieved by a meandering movement of the surface.

According to the invention, only the rolling elements classified as nondefective are used for the making of a roller bearing, while the other rolling elements are discarded. For example, the rolling elements classified as nondefective can be provided with a preservation treatment in order to avoid damage during the storage and processing of the rolling elements. Early inspection of the rolling elements is therefore also sensible because then rolling elements classified as defective can be directly discarded without being provided with a preservation treatment and without being stockpiled and transported.

In order to make possible a nondestructive transmission of the sound waves by the at least one ultrasound head to the rolling element during the ultrasound measurement, the ultrasound measuring device is preferably filled with liquid, and the rolling elements are dipped into the liquid for the ultrasound measurement.

Another subject matter of the invention is a rolling element inspection layout with an electronic control unit and at least one ultrasound measuring device, which is suitable in particular for performing the above described method, According to the invention, the ultrasound measuring device has a holder for individual rolling elements, at least one ultrasound head connected to the electronic control unit, and a drive unit for the movement of the individual rolling elements.

Basically it is conceivable that the individual rolling elements are inserted by hand each time individually into the ultrasound measuring device. Especially preferably, however, there is an automatic inspection of the rolling elements, for which a transport device is also provided. The transport device can have in particular a feed element connected to the electronic control unit Especially suited is a gripper, by which the individual rolling elements are inserted from a stockpile into the ultrasound measuring device and taken out of the ultrasound measuring device. But other feeding elements are also essentially conceivable. For example, it can also be provided that the rolling elements are brought up with suitable means to the ultrasound measuring device and then drop by their own weight, while for the removal of the inspected rolling elements an ejecting ram or the like operating from below on the rolling elements can be used As previously mentioned, the ultrasound measuring device is advisedly filled with liquid. This can be water, oil, a gel or the like, making possible a transmission of the ultrasound waves.

Especially preferably the ultrasound measuring device is arranged in a liquid basin, wherein also two or more ultrasound measuring devices each holding one rolling element can be arranged in the liquid basin. In this way it is possible to increase the throughput of the overall rolling element inspection layout, because the ultrasound measurement itself takes a certain amount of time, while the feeding and removal of the individual rolling elements by contrast can generally occur rather quickly.

In order to allow the fastest and most reliable possible ultrasound measurement, the ultrasound measuring device can have several, especially three ultrasound heads, which are arranged at an angle to each other. Besides a higher accuracy and reliability, such an arrangement can detect the total surface more quickly. In particular, several ultrasound measuring devices can be arranged in a common plane. With three ultrasound measuring devices, these can be arranged in the plane at an angle division of 45°, in which case for example one ultrasound head will be arranged precisely beneath the rolling element being inspected and another ultrasound head on each side at an angle of 45°.

The ultrasound heads are advisedly arranged so that the ultrasound waves produced impinge as, a central beam perpendicularly on the surface of the rolling element, in order to avoid an uncontrollable falsification of the measurement by reflections.

If the above described ultrasound measuring device has two noncylindrical drive rollers, a common axis of rotation of the drive rollers can be oriented perpendicular to the plane in which the ultrasound heads are arranged. When such an ultrasound measuring device is loaded with rolling elements of spherical shape, an alternating nonsynchronous driving of the two preferably conical or truncated conical drive rollers can produce a tumbling, especially a meandering movement of the surface, so that a complete inspection of the entire surface and the entire volume can be done especially quickly.

The method for the inspection of rolling elements is especially advantageous in the manufacturing of large roller bearings, because in this case especially large forces are acting on the individual rolling elements and the rolling elements due to their size can also be easily inspected by ultrasound. In addition, large roller bearings are also only maintained and replaced with great expense, for example, at wind power plants, so that an especially high reliability is demanded there.

Figure 2:
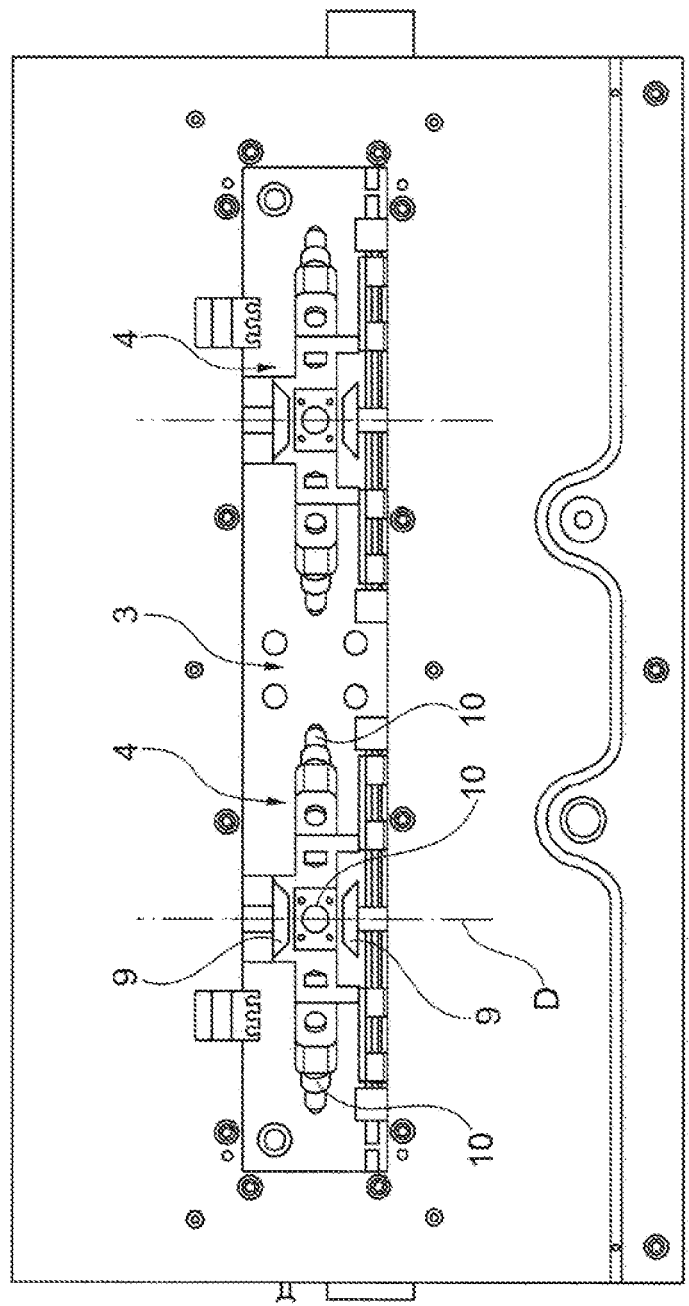

The invention will be explained below by bit means of only one sample embodiment shown by a drawing in which:

FIG. 1 schematically shows a rolling element inspection layout,

FIG. 2 schematically shows two ultrasound measuring devices arranged in a liquid basin of the rolling element inspection layout.

FIG. 1 shows in a schematic view a rolling element inspection layout for spherical rolling elements W. The spherical rolling elements W are loosely placed on a ball feed 1, with which the rolling elements W are broken up into single file. The individual rolling elements W are then picked up singly with a gripper 2 of a transport device and dipped into a liquid basin 3 with at least one ultrasound measuring device 4.

The liquid basin 3 is shown in detail in FIG. 2, there being two ultrasound measuring devices 4 provided in the sample embodiment, with which two rolling elements W can be inspected at the same time.

The rolling elements W are moved into the respectively assigned ultrasound measuring device 4 and subjected to an ultrasound measurement, wherein depending on the result of the ultrasound measurement the individual rolling elements W are classified as defective or nondefective.

The inspected rolling elements W are then taken out from the liquid basin 3 by the gripper 2 and delivered to a ball exit 5, The ultrasound measurement is evaluated by a central control unit 6, which also performs the corresponding classification of the individual rolling elements W as defective or nondefective. Rolling elements W classified as defective, i.e., especially rolling elements W with cracks, inclusions, cavities or the like, are rejected through a separate branch 7 of the ball exit 5, while the rolling elements W classified as nondefective are taken to a coating device 8, which provides the rolling elements W with a preservation treatment. For example, the preservation treatment can be applied with several spray heads.

The specific configuration of the ultrasound measuring device 4 arranged in the liquid basin 3 is shown in FIG. 2 in a top view. Each ultrasound measuring device 4 has two truncated conical drive rollers 9, which are configured and arranged in mirror symmetry with respect to a midplane and which can turn about a common axis of rotation D. Beneath the two drive rollers 9 in the sample embodiment there is a first ultrasound head 10, which is oriented perpendicularly. To the side of this there are two additional ultrasound measuring heads 10 in an orientation of 45° with respect to the horizontal. The ultrasound measuring heads 10 are arranged so that the ultrasound waves generated each time impinge as a central beam perpendicularly on the surface of the spherical rolling elements.

The two noncylindrical drive rollers 9 can be actuated variably and not synchronized by the control unit 6. A spherical rolling element W, which is set down on the drive rollers 9, can thus be turned in a tumbling movement in different directions, so that the entire surface of the spherical rolling element W can be surveyed in an especially fast and reliable manner with the three ultrasound heads 10. The rolling elements W can be held in their position by backstops, not shown.

The moving of the rolling elements W by the drive rollers 9 occurs through the control unit 6 according to a predetermined motion sequence, so that the entire surface as well as the entire volume accessible to an ultrasound inspection of the rolling elements is surveyed by the three ultrasound heads 10.

The rolling element inspection layout can be configured so that the individual rolling elements roll onward by themselves, with the exception of the transport of the spherical rolling elements W with the gripper 2. The rolling elements W classified as defective can be taken for example through the corresponding branch 7 of the ball exit for their disposal in a collection container. On the other hand, the rolling elements classified as nondefective roll through the coating device 8 and are provided there with a coating in the form of a preservation treatment. For example, three spray nozzles can be provided here, each arranged with an offset of 90° to each other, above and to the side of the designated path of the rolling elements W, in order to enable a total wetting with the preservation treatment.

What is claimed is:

1. A method for inspection of rolling elements by means of ultrasound comprising:
   individually taking the rolling elements to an ultrasound measuring device, wherein the rolling elements are of spherical shape;
   arranging the individual rolling elements in a center between two drive rollers of the ultrasound measuring device;
   moving the individual rolling elements in the ultrasound measuring device and subjecting the individual rolling elements to an ultrasound measurement,
      wherein in the moving step, the drive rollers are turned with a same speed and in a same direction about a common axis of rotation, such that the individual rolling elements placed thereupon are also turned about an axis arranged parallel to the common axis of rotation of the drive rollers, and such that a circumferential line of the individual in rolling elements is moved past a stationary ultrasound head,
      wherein after a complete rotation, an opposite running drive of the drive rollers produces a rotation of the individual rolling elements about a vertical axis, and
      wherein during another synchronous rotation of the drive rollers, a different circumferential line in a manner of a circle of longitude is moved past an assigned measuring device; and
   classifying the individual rolling elements, depending on a result of the ultrasound measurement the individual rolling elements, as defective or nondefective.

2. The method as claimed in claim 1, wherein the method includes examining individual rolling elements with at least two ultrasound heads in the ultrasound measuring device.

3. The method as claimed in claim 1, wherein the method includes turning the individual rolling elements in different directions during the ultrasound measurement.

4. The method as claimed in claim 1, wherein the method includes providing the individual rolling elements classified as nondefective with a preservation treatment.

5. The method as claimed in claim 1, wherein the method includes filling the ultrasound measuring device with liquid and dipping the individual rolling elements into the liquid for the ultrasound measurement.

6. The method as claimed in claim 1, wherein the two drive rollers are located in parallel next to each other.

7. A rolling element inspection layout comprising an electronic control unit and an ultrasound measuring device,
   wherein the ultrasound measuring device has a holder for individual rolling elements, at least one ultrasound head connected to the electronic control unit, and a drive unit for the movement of the individual rolling elements,
   wherein the individual rolling elements are of spherical shape,
   wherein the individual rolling elements are arranged in a center between two drive rollers,
   wherein the drive rollers are turned with a same speed and in a same direction about a common axis of rotation with the drive unit such that the individual rolling elements placed thereupon are also turned about an axis arranged parallel to the common axis of rotation of the drive rollers, and such that a circumferential line of the individual rolling elements are moved past a stationary ultrasound head,
   wherein after a complete rotation, an opposite running drive of the drive rollers produces a rotation of the individual rolling elements about a vertical axis,
   wherein during another synchronous rotation of the drive rollers, a differential circumferential line in a manner of a circle of longitude is moved past an assigned measuring device.

8. The rolling element inspection layout as claimed in claim 7, wherein a transport device is provided for the transport of the individual rolling elements, which has at least one feed element connected to the electronic control unit.

9. The rolling element inspection layout as claimed in claim 7, wherein the ultrasound measuring device is arranged in a liquid basin.

10. The rolling element inspection layout as claimed in claim 9, wherein at least two ultrasound measuring devices each holding one rolling element are arranged in the liquid basin.

11. The rolling element inspection layout as claimed in claim 7, wherein the ultrasound measuring device has at least two ultrasound heads arranged at an angle to each other.

12. The rolling element inspection layout as claimed in claim 11, wherein the ultrasound measuring device has three ultrasound heads arranged at an angle to each other.

13. The rolling element inspection layout as claimed in claim 7, wherein the ultrasound measuring device has two noncylindrical drive rollers.

14. The rolling element inspection layout as claimed in claim 13, wherein the drive rollers have a common axis of rotation, which is perpendicular to a plane in which the at least one ultrasound head is arranged.

15. The rolling element inspection layout as claimed in claim 7, wherein the ultrasound measuring device is followed by a coating device for a preservation treatment of the individual rolling elements.

16. The rolling element inspection layout as claimed in claim 7, wherein the two drive rollers are located in parallel next to each other.

* * * * *

UNITED STATES PATENT AND TRADEMARK OFFICE
CERTIFICATE OF CORRECTION

PATENT NO. : 10,190,943 B2
APPLICATION NO. : 14/905466
DATED : January 29, 2019
INVENTOR(S) : Martin Eckey et al.

Page 1 of 1

It is certified that error appears in the above-identified patent and that said Letters Patent is hereby corrected as shown below:

In the Claims

Column 5, Line 66, delete "in" after "of the individual"

Signed and Sealed this
Second Day of April, 2019

Andrei Iancu
*Director of the United States Patent and Trademark Office*